United States Patent [19]

Davies et al.

[11] 4,213,916
[45] Jul. 22, 1980

[54] CONVERSION OF STEREOISOMER INTO ITS DIASTEREOISOMER

[75] Inventors: John H. Davies; Basil T. Grayson, both of Canterbury; Herbert P. Rosinger, Sittingbourne, all of England

[73] Assignee: Shell Internationale Research Maatschappij B.V., The Hague, Netherlands

[21] Appl. No.: 914,571

[22] Filed: Jun. 9, 1978

[30] Foreign Application Priority Data

Jun. 13, 1977 [GB] United Kingdom ............... 24612/77

[51] Int. Cl.² ................. C07C 121/66; C07C 121/75
[52] U.S. Cl. .................... 260/465 D; 424/304
[58] Field of Search ................... 260/465 D

[56] References Cited

U.S. PATENT DOCUMENTS

| 4,061,644 | 12/1977 | Wood | 260/465 D |
| 4,133,826 | 1/1979 | Warnant et al. | 260/465 D |

FOREIGN PATENT DOCUMENTS 853866 10/1977 Belgium.
853867 10/1977 Belgium.
856195 10/1977 Belgium.

OTHER PUBLICATIONS

Dale et al., *J. Amer. Chem. Soc.*, 90:14, pp. 3732–3738 (1968).
Hauser et al., *J. Amer. Chem. Soc.*, 95(13), pp. 4345–4348 (1958).
Howe et al., *Chemical Abstracts*, vol. 79, 52682z (1973).
Smejkal et al., *Chemical Abstracts*, vol. 59, 7396d (1963).
Weidmann et al., *Chemical Abstracts*, vol. 67, 21352q (1967).

*Primary Examiner*—Dolph H. Torrence
*Attorney, Agent, or Firm*—Pravel, Gambrell, Hewitt, Kirk, Kimball & Dodge

[57] ABSTRACT

A process for the conversion of a stereoisomer into its diastereoisomer of a compound having the following general formula:

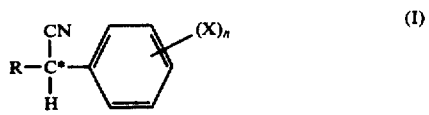

(wherein the asterisk denotes an asymmetric carbon atom; each X is individually hydrogen, alkyl, aryl, alkaryl, aralkyl, alkoxy, aryloxy, halogen, nitro, hydroxy or cyano; R is an organic residue containing one or more centers of asymmetry; and n is 1 to 5), which comprises subjecting the said stereoisomer to the action of an alkali metal carbonate and an inert polar solvent at a temperature in the range 20° to 100° C. and physically separating the required diastereoisomer from the resulting mixture of diastereoisomers.

7 Claims, No Drawings

CONVERSION OF STEREOISOMER INTO ITS DIASTEREOISOMER

This invention relates to a process for the conversion of a stereoisomer of a compound containing an asymmetric benzylic carbon atom into its diastereoisomer.

Frequently, pesticidally-active and pharmaceutically-active compounds have one or more asymmetric carbon atoms in their structures and, again, frequently one or a combination of the resulting stereoisomers is more biologically active than the remaining isomer or isomers. To achieve the best biological effect it is desirable to isolate the most active isomer or combination of isomers. Isolation of the desired isomer may be achieved by means of physical separation or by chemical modification followed by physical separation, but whichever method is adopted the less active isomer or isomers invariably remain. The Applicant has now found a convenient route for converting the unwanted stereoisomer into the desired diastereoisomer of compounds containing an asymmetric benzylic carbon atom.

Accordingly, the present invention provides a process for the conversion of a stereoisomer into its diastereoisomer of a compound having the following general formula:

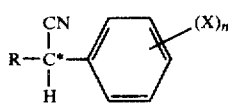

(I)

(wherein the asterisk denotes an asymmetric carbon atom; each X is individually hydrogen, alkyl, aryl, alkaryl, aralkyl, alkoxy, aryloxy, halogen, nitro, hydroxy or cyano; R is an organic residue containing one or more centres of asymmetry; and n is 1 to 5), which comprises subjecting the said stereoisomer to the action of an alkali metal carbonate and an inert polar solvent at a temperature in the range 20° to 100° C., preferably 20° C. to 80° C. and physically separating the required diastereoisomer from the resulting mixture of diastereoisomers.

Provided the organic residue denoted by R has at least one centre of asymmetry its chemical constitution is unimportant and the process according to the invention will proceed satisfactorily so long as there are no reactive groups or sites in the residue which will interfere with the reagents employed. The Applicant has found the process to be of particular importance when R represents an optionally-substituted cyclopropane carboxylic acid residue or an optionally-substituted phenylacetic acid residue.

When R represents an optionally-substituted cyclopropane carboxylic acid residue it preferably has the following general formula:

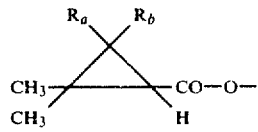

(II)

wherein $R_a$ and $R_b$ both represent an alkyl group having from 1 to 6 carbon atoms, especially methyl, or a halogen, especially chlorine, atom; or $R_a$ and $R_b$ together represent an alkylene group having from 2 to 6, especially 3, carbon atoms; or $R_a$ represents a hydrogen atom and $R_b$ represents an alkenyl group having from 2 to 6 carbon atoms, especially an isobutenyl group, or a haloalkenyl group having from 2 to 6 carbon atoms and from 1 to 3 fluorine, chlorine or bromine atoms, especially a mono- or dichloro-vinyl group, or a mono- or dibromo-vinyl group; with the proviso that when one of $R_a$ and $R_b$ represent a methyl group the other does not.

When R represents an optionally-substituted phenyl acetic acid residue it preferably has the following general formula:

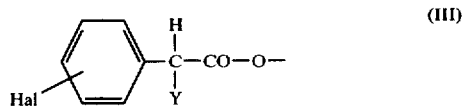

(III)

wherein Hal represents a halogen, preferably chlorine, atom, and Y represents an alkyl group of 1 to 6 carbon atoms, especially a branched chain group such as an isopropyl group.

In the general formula I substituent X is preferably a hydrogen, chlorine, fluorine or bromine atom, an alkyl or alkoxy group of 1 to 4 carbon atoms, a phenyl or phenoxy group, a phenylalkyl or alkylphenyl group of up to 10 carbon atoms, or a nitro, hydroxy or cyano group. Especially preferred are the compounds of general formula I wherein X is phenoxy, benzyl or halogen such as chlorine, and n is 1.

Because of their very effective pesticidal activity and because there is a need to convert the less-active stereoisomer into the more-active diastereoisomer or diastereoisomers, the conversion process according to the invention is particularly useful when applied to the following compounds:

[R]-alpha-cyano-3-phenoxybenzyl(1R, cis)-2,2-dimethyl-3-(2,2-dibromovinyl) cyclopropane carboxylate;

[R]-alpha-cyano-3-phenoxybenzyl(1R, cis)-2,2-dichlorovinyl-3,3-dimethyl cyclopropane carboxylate;

[R]-alpha-cyano-3-phenoxybenzyl 2,2-dimethylvinyl-3,3-dimethyl cyclopropane carboxylate;

[R]-alpha-cyano-3-phenoxybenzyl(1R, trans)-2,2-dimethyl-3-spirocyclobutane-cyclopropane carboxylate; and [R]-alpha-cyano-3-phenoxybenzyl[S]-2-(4-chlorophenyl)-2-isopropylacetate.

The inert polar solvent used in the process according to the invention may be a halogenated hydrocarbon, for example, chloroform, methylene chloride, carbon tetrachloride and perchloroethylene, or an ether for example diethyl ether, dioxane, dibutyl ether and tetrahydrofuran, or an alkanol, for example ethanol or isopropanol. Very good results have been obtained with ethanol or chloroform.

The alkali metal carbonate is preferably sodium carbonate.

As a result of the action of the solvent and the alkali metal carbonate, the resulting mixture usually produces a diastereoisomer mixture comprising the starting stereoisomer and its diasterioisomer. Any established physical separation technique for obtaining the desired isomer from the mixture may be employed, for example fractional crystallisation or chromatographic separation. As is well-known in crystallisation and separation techniques of this sort a search is required for the best possible solvent from which the desired isomer can be readily crystallised. In the case of the compound of general formula I wherein R is (1R, cis)-2,2-dimethyl-3-(2,2,-dibromovinyl)-cyclopropylcarbonyloxy, X is 3-phenoxy and n=1, the desired isomer readily crystallises from the mixture if hexane is employed as the crystallisation solvent. Further details of this particular crystallisation technique are given in the Examples.

The process according to the invention is further illustrated by the following Example. The nomenclature used in this application to describe the spatial configuration of the isomers of cyclopropane carboxylic acid esters is the so-called Elliott nomenclature as given in M. Elliott, A. W. Farnham, N. F. Janes, P. H. Needham and D. A. Pulman, Nature, 1974, 248, 710.

EXAMPLE

Conversion of [R]-alpha-cyano-3-phenoxybenzyl-(1R, cis)-2,2-dimethyl-3-(2,2-dibromovinyl)cyclopropanecarboxylate into the corresponding [S], (1R cis) form In this example the following compound in which the acid portion is in the (1R, cis) form was used, each asymmetric carbon atom being denoted by an asterisk:

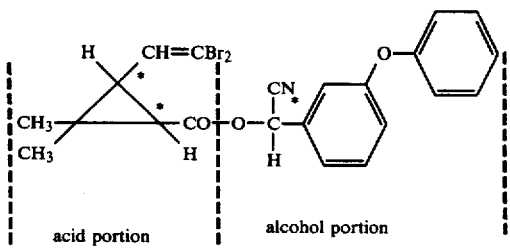

Since the spatial configuration of the acid portion of the molecule is fixed, it follows that the compound has 2 stereoisomers by virtue of the asymmetric benzylic carbon atom in the alcohol portion; in this Example, the 2 isomers and their mixture have been given the following references:

| Isomer Reference | Absolute Configuration of Alcohol Portion | Absolute Configuration of Acid Portion |
|---|---|---|
| Isomer R | R | (1R, cis) |
| Mixture SR | S,R | (1R, cis) |
| Isomer S | S | (1R, cis) |

In terms of pesticidal activity Isomer S is more active than its stereoisomer Isomer R and thus there is considerable incentive, after removal of the desired Isomer S from the Mixture SR, to convert the R isomer into the S-form. This example demonstrates that such a conversion can be readily achieved without interfering with the (1R, cis) configuration of the acid portion of the compound.

20 g Isomer R (0.04 mole) was dissolved in 1000 ml dioxane and 50 ml N-sodium carbonate was added with stirring. The reaction mixture was heated to 50° C. for 4½ hours. Most of the dioxane was removed on a rotary evaporator at room temperature and 1000 ml water was added; the product was extracted with methylene chloride, the water washed methylene chloride solution dried over anhydrous sodium sulphate and the solvent removed. The residue was degassed at high vacuum to constant weight yielding 20 g (100% recovery) of Mixture RS consisting of 30% Isomer S and 70% Isomer R. The residue was recrystallised from hexane. This gave 4.0 g of Isomer S and 15.2 of mother liquor containing mainly Isomer R.

After removal of the hexane from the mother liquor Isomer R was redissolved in chloroform as above, treated with 3 ml of dry triethylamine, heated as before, and was reconverted to Mixture SR. From this by treatment as before with hexane another 1.0 of Isomer S was isolated. The mother liquor from this could of course be treated again.

What we claim is:

1. A process for the conversion of a stereoisomer into its diastereoisomer of a compound having the following general formula:

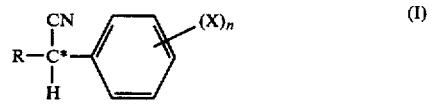

wherein the asterisk denotes an asymmetric carbon atom; n is 1 to 5; each X is independently a hydrogen, chlorine, fluorine or bromine atom, an alkyl or alkoxy group of 1 to 4 carbon atoms, a phenyl or phenoxy group, a phenylalkyl or alklphenyl group of up to 10 carbon atoms, or a nitro, hydroxy or cyano group; R is an organic residue containing one or more centres of asymmetry and is selected from:

(a) a cyclopropane carboxylic acid residue having the following general formula:

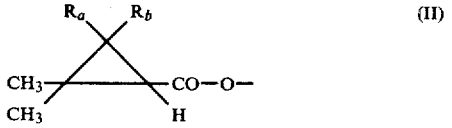

wherein $R_a$ and $R_b$ both represent an alkyl group having from 1 to 6 carbon atoms; or $R_a$ and $R_b$ together represent an alkylene group having from 2 to 6 carbon atoms; or $R_a$ represents a hydrogen atom and $R_b$ represents an alkenyl group having from 2 to 6 carbon atoms and from 1 to 3 fluorine, chlorine or bromine atoms; with the provision that when one of $R_a$ and $R_b$ represent a methyl group the other does not, and (b) a phenyl acetic acid residue having the following general formula:

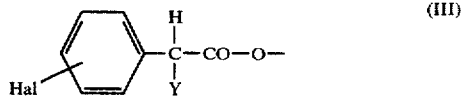

wherein Hal represents a halogen atom, and Y represents an alkyl group of 1 to 6 carbon atoms; which process comprises subjecting the said stereoisomer to the action of an alkali metal carbonate and an inert polar solvent at a temperature in the range 20° to 100° C. to effect conversion of configuration at the carbon atom denoted by the asterisk without interfering with one or more centres of asymmetry in R, and physically separating the required diastereoisomer from the resulting mixture of diastereoisomers.

2. A process according to claim 1 wherein the temperature range is 20° to 80° C.

3. A process according to claim 1 or 2 wherein X is phenoxy, benzyl or halogen and n is 1.

4. A process according to claim 1 wherein the solvent is chloroform, methylene chloride, carbon tetrachloride, perchloroethylene, diethyl ether, dioxane, dibutyl ether, tetrahydrofuran, ethanol or isopropanol.

5. A process according to claim 1 wherein the base is sodium carbonate.

6. A process according to claim 1 wherein the required diastereoisomer is separated from the mixture of diastereoisomers by fractional crystallisation or chromatographic separation.

7. A process according to claim 1 or 2 wherein the compound of general formula I is:

[R]-alpha-cyano-3-phenoxybenzyl(1R, cis)-2,2-dimethyl-3-(2,2-dibromovinyl) cyclopropane carboxylate;

[R]-alpha-cyano-3-phenoxybenzyl(1R, cis)-2,2-dichlorovinyl-3,3-dimethyl cyclopropane carboxylate;

[R]-alpha-cyano-3-phenoxybenzyl 2,2-dimethylvinyl-3,3-dimethyl cyclopropane carboxylate;

[R]-alpha-cyano-3-phenoxybenzyl(1R, trans)-2,2-dimethyl-3-spirocyclobutane cyclopropane carboxylate; or

[R]-alpha-cyano-3-phenoxybenzyl [S]-2-(4-chlorophenyl)-2-isopropyl-acetate.

* * * * *